United States Patent
Guo (10) Patent No.: US 8,465,449 B2
(45) Date of Patent: Jun. 18, 2013

(54) PISTON-TYPE BREAST PUMP

(75) Inventor: Paul Wen Guo, Guangdong (CN)

(73) Assignee: Shenzhen Siyong Technology Ltd., Shenzhen, Guangdong (CN)

( * ) Notice: Subject to any disclaimer, the term of this patent is extended or adjusted under 35 U.S.C. 154(b) by 214 days.

(21) Appl. No.: 13/138,085

(22) PCT Filed: Nov. 13, 2009

(86) PCT No.: PCT/CN2009/074944
§ 371 (c)(1),
(2), (4) Date: Jun. 30, 2011

(87) PCT Pub. No.: WO2010/091580
PCT Pub. Date: Aug. 19, 2010

(65) Prior Publication Data
US 2011/0270162 A1    Nov. 3, 2011

(30) Foreign Application Priority Data
Feb. 15, 2009  (CN) ...................... 2009 2 0006204 U (51) Int. Cl.
*A61M 1/06*    (2006.01)
(52) U.S. Cl.
USPC .......................................... 604/74

(58) Field of Classification Search
USPC ............. 604/73, 74, 151, 152, 346, 118, 119, 604/120, 121
See application file for complete search history.

(56) References Cited

U.S. PATENT DOCUMENTS

| | | | |
|---|---|---|---|
| 5,007,899 A * | 4/1991 | Larsson | 604/74 |
| 5,720,722 A * | 2/1998 | Lockridge | 604/74 |
| 6,045,529 A * | 4/2000 | Nuesch | 604/74 |
| 2004/0127845 A1* | 7/2004 | Renz et al. | 604/74 |
| 2008/0009815 A1* | 1/2008 | Grabenkort et al. | 604/346 |

* cited by examiner

*Primary Examiner* — Matthew F Desanto
(74) *Attorney, Agent, or Firm* — Novoclaims Patent Services, LLC; Mei Lin Wong (57) ABSTRACT

A piston-type breast pump includes a piston-type pumping device, a DC motor, a gear reducer, and a control circuit board arranged in a housing. A gears rocking block (12) is connected with the piston-type pumping device, and far-near points induction chips and a buffering spring are provided between the block (12) and the reducer. A journey induction wheel is arranged at the motor shaft. A speed adjustment knob (35), a journey adjustment knob (34), a fast suck galactagogue button (33), and a suction adjustment screw are provided at the outer surface of the housing. The main body of the breast pump is a vertical design, and is constructed with a recessed bottle location (37), and the bottle holder (36) is removable.

16 Claims, 5 Drawing Sheets

FIG. 5

PISTON-TYPE BREAST PUMP

CROSS-REFERENCE TO RELATED APPLICATIONS

This application claims priority, and is a U.S. National Phase (37 USC Section 371) of International Application No. PCT/CN2009/074944, filed Nov. 13, 2009, entitled PISTON-TYPE BREAST PUMP, which claims the benefit of CN Application No. 200920006204.0 filed Feb. 15, 2009, the contents of which are expressly incorporated herein by reference.

BACKGROUND OF THE PRESENT INVENTION

1. Field of Invention

The present invention relates to a breast pump for human, and more particularly to a piston-type breast pump for human.

2. Description of Related Arts

Conventional breast pumps are divided into two types, the membrane type or the piston type. The membrane type has a simple structural construction and is easy to use. However, the drawbacks are low flow volume and low efficiency, low pressure level, and requirement of fast pressing in order to generate intermittent vacuum condition. Manual operation will lead to tiredness of user, especially the hands. Electric operation fails to provide a rhythmic and sufficient sectional force for producing a suction effect, and the effect as produced is greatly different from a frequency of a suction effect of a baby.

Piston-type breast pump has a greater stroke for the process and produce an effect which is more similar to a suction frequency of a baby. In view of suction force and efficiency, user complains about insufficient suction force and low efficiency for those marketed products. For some products, the suction force is large when tested without milking bottle kits but insufficient in actual use.

On the other hand, piston-typed breast pump with high suction power is usually bulky and large in size which is not suitable for carriage, while those with compact size are of low suction power. In addition, the piston-type breast pump usually comes with problems of noise and vibration. In view of function, there is no such multi-functional breast pump which is adjustable for controlling speed, stroke of the process, or is capable of simulating a lactation promotion process, and provides overall suction power adjustment. In short, a breast pump which is high efficiency, high power, small size, silent, and controllable for multi-function still does not exist. . SUMMARY OF THE PRESENT INVENTION The invention is advantageous in that it provides a piston-type breast pump which has improved functions of which the breast pump has a small size, high efficiency, high suction force, low noise level and low vibration level while providing multi-functional modes.

Additional advantages and features of the invention will become apparent from the description which follows, and may be realized by means of the instrumentalities and combinations particular point out in the appended claims.

According to the present invention, the foregoing and other objects and advantages are attained by a piston-type breast pump which includes a housing and a piston-type pumping arrangement received in the housing, comprising a DC motor, a gear reducer and a control circuit which are received in the housing; a gear swing unit operatively communicated with the gear reducer and connected to the pumping arrangement; first and second position sensor plates for detecting a far point position and a near point position respectively provided between the gear swing unit and the gear reducer; a buffer spring connected to the gear swing unit; a stroke sensor wheel positioned on an axis member of the DC motor; a speed control button, process control button, a promoting lactation button and a suction adjustment screw positioned on an outer side of the housing; wherein the housing has a vertical design having an indented portion defining a bottle side support on the housing and comprising a bottle bottom support provided thereon in a detachable manner.

The housing comprises a front housing member, a rear housing member and a bottom housing member for forming the housing, wherein the speed control button, the process control button and the promoting lactation button are provided on the front housing member and communicatively connected to the control circuit, wherein the bottle side support is constructed into a semicircle structure having a bottom end operatively connected with the bottle bottom support for retaining a milk bottle into position, wherein the front housing member further provides an output head arranged for connecting to the milk bottle through a bottle connecting tube, wherein the suction adjustment screw is positioned on the rear housing member.

The gear reducer comprises an axis support connected to the bottom housing member; a first axis, a second axis, a gear swing core axis positioned and supported in sequence through an inclined surface defined through a supporting side of the axis support; a gear connected to a middle portion of the first axis; a gear pulley connected to an end portion of the first axis; a second gear provided to a middle portion of the second axis operatively connected to the gear of the first axis, a third gear provided at one end portion of the second gear complementary to a teeth surface of the gear swing unit; a gear swing axis provided at one end of the gear swing unit through which the piston-typed pumping arrangement is connected; a motor pulley connected to the gear pulley through a belt arranged for connecting the gear pulley to the DC motor, wherein the gear has a size smaller than the second gear, and the second gear has a size larger than the third gear.

The piston-typed pumping arrangement comprises a cylinder defining a cylinder cavity, a piston unit operatively provided in the cylinder cavity; and an output tube and a connecting output provided at one end portion of the cylinder, wherein the output tube is connected to an output head of the front housing member, wherein a frame unit is connected to the bottom housing member while a control valve such as a throttle valve is supported through and provided on the frame unit, wherein the end portion of the cylinder is connected to the frame unit in a hinged manner, wherein the control valve is connected to the connecting output through the output tube.

The bottle bottom support comprises a connecting leg and a position member, wherein the housing has a position groove and a connecting hole corresponding to a position of the connecting leg and the position member respectively, wherein the connecting leg has a position hole and an inclined surface provided thereon.

The buffer spring is inserted to connecting to the gear swing core axis in an enclosed manner, wherein the buffer spring has two ends defining to force receiving portions which are provided to the gear swing unit and to the axis support respectively.

Two photoelectric sensors are positioned corresponding to the first and second position sensor plates respectively in which the first and second position sensor plates have a protruded structural construction. One of the first and second position sensor plates is inserted into one of the grooves of the photoelectric sensor corresponding to the position sensor plates when the gear swing unit swings to a position corresponding to the particular position sensor plate for detecting a position of the gear swing unit.

The stroke sensor wheel and the motor pulley are connected, wherein the stroke sensor wheel has two indented portions, wherein the stroke sensor wheel comprises photoelectric sensor corresponding to the stroke sensor wheel.

The throttle valve has a valve body, a valve core and a suction adjustment screw for forming the throttle valve, wherein the valve core has a cone structure at a first end and a plurality of thread construction at second end opposite to the first end, wherein the valve body has a core receiving cavity arranged for receiving and connecting the valve core, wherein the valve body has an input opening and an output opening which are channeled through the core receiving cavity respectively, wherein the valve body is supported by the frame unit, wherein the suction adjustment screw is connected with the valve core and extended to penetrate to an outer side of the rear housing member, wherein the input opening is connected to the connecting output through a tube.

The housing has a vertical design, which is, the piston suction arrangement, the gear reducer and the DC motor are orderly arranged in a vertical manner.

The preferred embodiment of the present invention employs a low speed high power DC motor for providing driving force, a gear swing unit driving the forward and backward motion of the piston through a two-stage gear reducer, a buffer spring between the gear swing unit and the reducer arrangement, thereby the overall size is compact, while the suction force is large and the vibration and noise level are reduced.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

The preferred embodiment of the present invention is further described in details with the following drawings.

DETAILED DESCRIPTION OF THE PREFERRED EMBODIMENT

Figure 1:
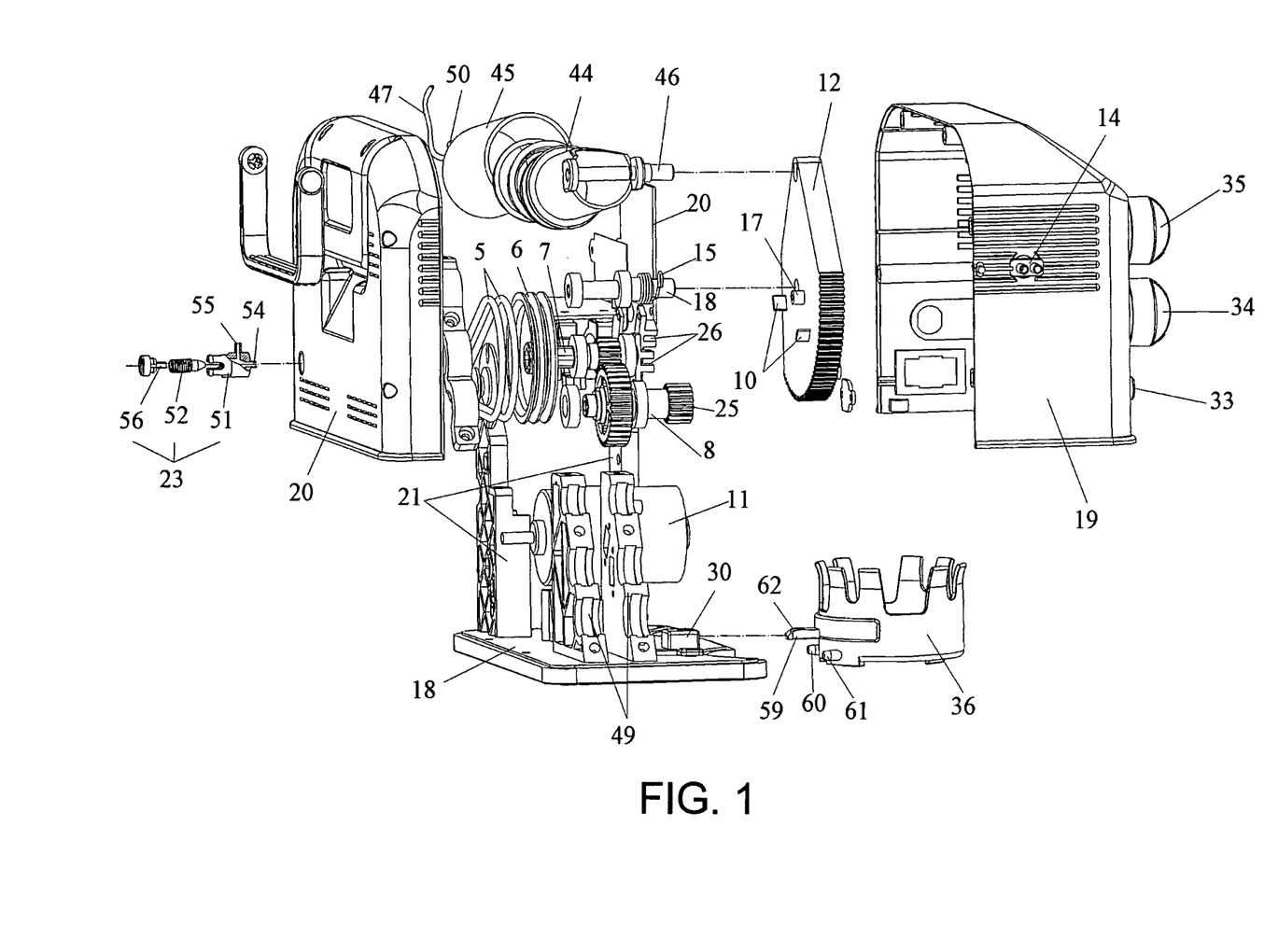
FIG. 1 is an exploded view of a piston-type breast pump according to a preferred embodiment of the present invention.
Figure 3:
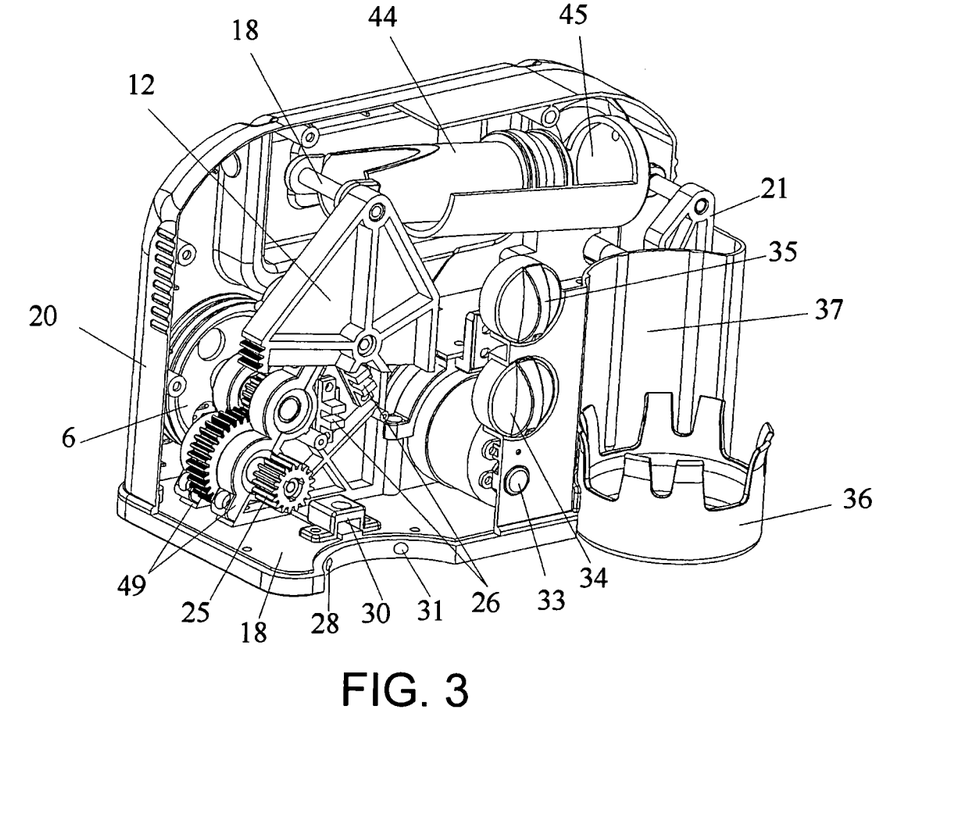
FIG. 3 is a front perspective view of a piston-type breast pump according to the above preferred embodiment of the present invention.
Figure 4:
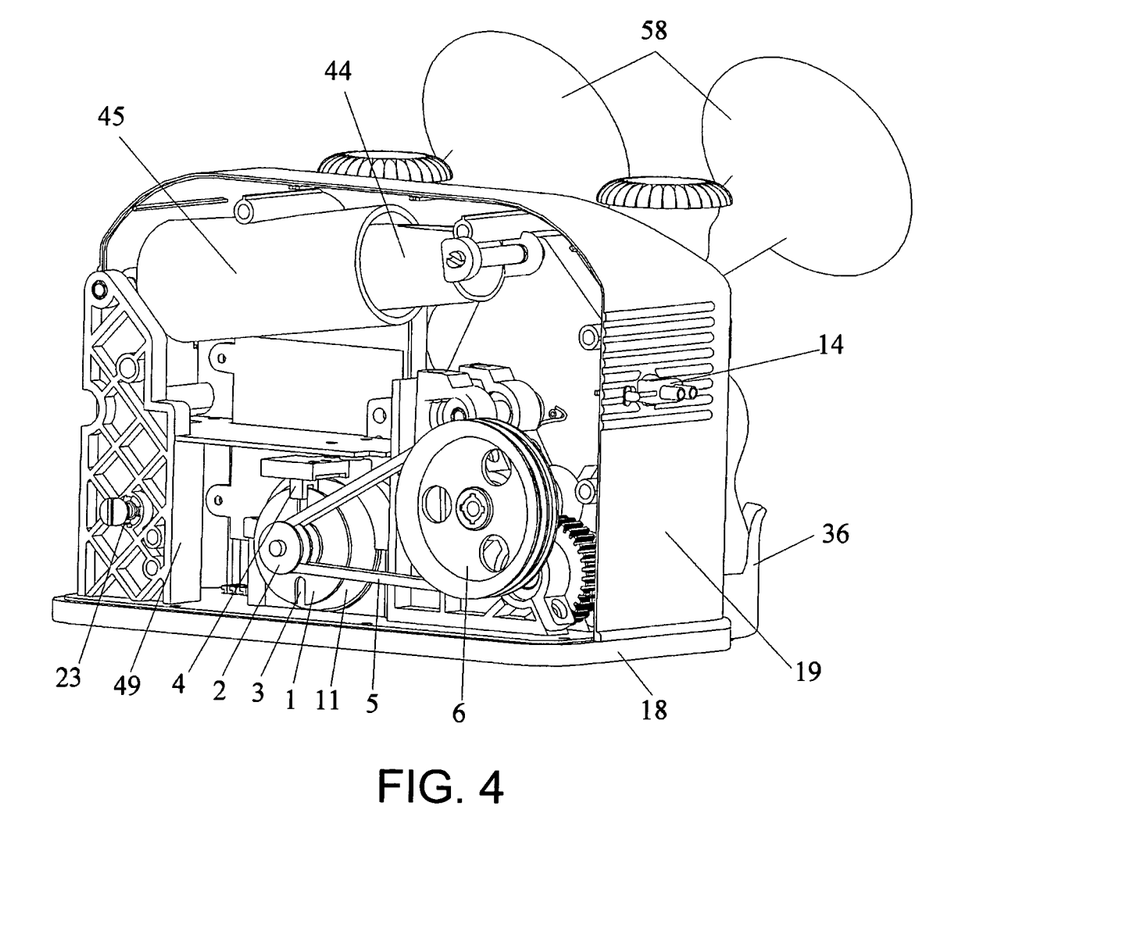
FIG. 4 is a rear perspective view a piston-type breast pump of FIG. 2 according to the above preferred embodiment of the present invention.

Referring to FIGS. 1, 3 and 4 of the drawings, a piston-type breast pump according to a preferred embodiment of the present invention, includes a transmission arrangement. The transmission arrangement includes a DC motor 11 having a motor axis, a motor pulley 2 coaxially connected to the DC motor 11 through the motor axis having two grooves, a gear pulley 6 driven by the motor pulley 2 in which two belts are provided on the two grooves respectively to drive the gear pulley 6, a small gear, namely a first gear, defining a first axis 7 and connecting to the gear pulley through the first axis 7 of the first gear, a large gear, namely a second gear, defining a second axis 8 which is driven by the first gear through the first axis 7, a small gear, namely a third gear 25, connecting to the second gear through one end of the second axis 8, and a gear swing unit 12 cooperatively connected with the third gear 25 in a gear-wheel manner. Preferably, an overall size of the transmission arrangement is minimized through presetting the transmission ratio of motor pulley to gear pulley, the transmission ratio of the first gear to the second gear, and the transmission ratio of the third gear 25 to the gear swing unit 12. In particular, the three axes of the transmission arrangement, which are the motor axis, the first axis and the second axis, are aligned in one inclined plane for reducing the size and facilitating installation or assembly.

Referring to FIGS. 1, 3 and 4 of the drawings, the piston-type breast pump according to a preferred embodiment of the present invention includes a cylinder 45, a frame unit 21 supporting the cylinder 45 in a suspending manner, a piston unit 44 pulling the cylinder 45 such that a vacuum condition is generated for the cylinder 45, an output tube 47 connected to one end of the cylinder 45, a housing comprising an output head 14 which is connected to the output tube 47, a gear swing axis 46 of the gear swing unit 12 connected to the piston unit 44 in a suspending manner. The DC motor 11 drives the piston unit in a reciprocal and rotational manner, pushing the cylinder 45 to generate the vacuum condition adapted for providing an output through the output tube 47 and the output head 14.

Referring to FIGS. 1 and 3 of the drawings, the piston-type breast pump according to a preferred embodiment of the present invention includes an axis support 49 supporting the DC motor 11, a first and a second photoelectric sensors 26 positioned between the axis support 49 and the gear swing unit 12, a first and a second position sensor plates 10 extended from the gear swing unit 12 corresponding to the first and the second photoelectric sensors 26 respectively defining a near point position at which the cylinder is at a first position and a far point position at which the cylinder is at a second position, and a control circuit. The gear swing unit 12 starts to rotate when the cylinder 45 is returned to the first position, thereby a first position sensor plate 10 is inserted into a first photoelectric sensor 26 and the DC motor 11 is initiated to having a forward rotational movement through the control circuit. Likewise, the gear swing unit 12 starts to rotate when the cylinder 45 is returned to the second position, thereby the second position sensor plate 10 is inserted into the second photoelectric sensor 26 and the DC motor 11 is initiated to having a backward rotational movement through the control circuit. Accordingly, the cylinder 45 is controlled to move to the first and the second positions in a controllable manner.

As shown in FIGS. 1 and 4 of the drawings, the motor pulley 2 is installed onto the motor axis of the DC motor 11, and a stroke sensor wheel 1 affixed on the motor pulley 2. The stroke sensor wheel 11 has two indented portions 3. The DC motor 11 has a photoelectric sensor 4 provided on a cover portion of the DC motor 11. The stroke sensor wheel 11 is arranged for rotating between two opposite poles of the photoelectric sensor 4. The control circuit initiates a counting module thereof if the indented portion 3 detects the photoelectric sensor 4, wherein ½ rotation cycle is counted for each detection. The cylinder 45 can be controlled through controlling a total rotation cycle of the DC motor, thereby an output value of vacuum level is controlled. The rotation cycle of the DC motor is adjusted through a stroke control button 34 to adjust a position of a potentiometer corresponding to an output of the stroke control button 34. The control circuit reads an output voltage of the potentiometer which is corresponding to a continuous rotational cycle of the DC motor. The stroke sensor wheel 2 has two indented portions so as to increase a control level of stroke motion in a dedicate and accurate manner, such that a user will not easily sense a jumping motion between different level of stroke motion. The sensor is positioned on the motor axis of the DC motor, compared to positioning on the cylinder, an accuracy of the stroke motion is increased while the overall size is minimized.

Figure 5:
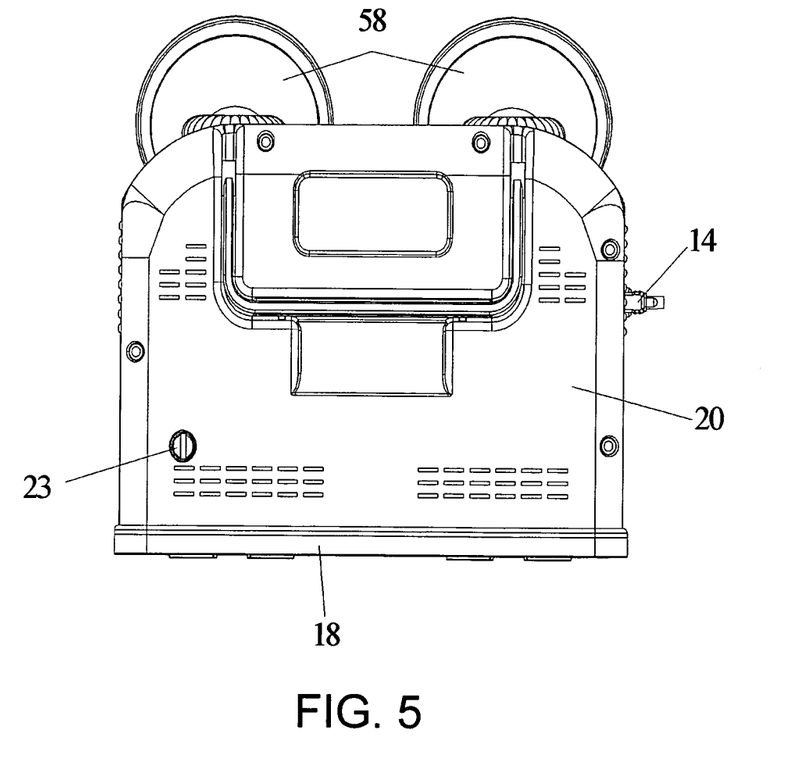
FIG. 5 is a rear perspective view of a piston-type breast pump according to the above preferred embodiment of the present invention.

Referring to FIG. 1 of the drawings, the cylinder further includes a connecting output 50 connecting to a control valve 23 (which is a throttle valve) through a connecting tube. The control valve 23 has a valve body 51, a valve core 52 and a suction adjustment screw 56. The valve core 52 has a cone structure at one end connecting to the valve body 51. The valve body 51 has an input opening 54 and an output opening 55. Ventilation flow is provided through a level of opening between the valve body 51 and the cone structure of the valve core 52. The valve body 51 is provided on the frame unit 21. The valve core is connected to the suction adjustment screw 56 to penetrate outside a rear housing member 20 of the housing, which is shown in FIG. 5. The control valve 23, which is connected to the cylinder 45, is arranged for adjusting an overall suction force of the breast pump, thereby providing a suction adjustment feature in additional to the stroke control, which is very useful to provide flexibility to fit the different users who may have different preferences for stroke frequency or level of suction force. When the control valve 23 is tightened, the cylinder 45 under a particular preset stroke level will provide the maximum suction force. When the control valve 23 is loosen, the suction force will be reduced because of air passage and the level of suction force is proportional to the degree of opening of the control valve 23.

Figure 2:
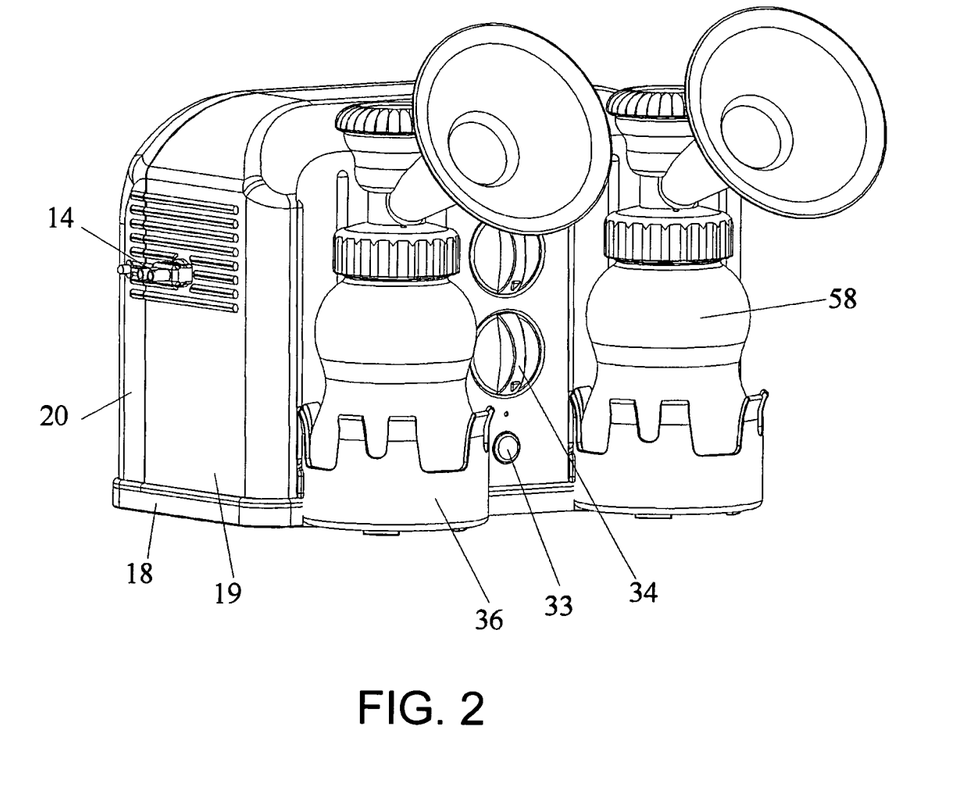
FIG. 2 is an illustration of a piston-type breast pump after assembly according to the above preferred embodiment of the present invention.

Referring to FIGS. 1, 2 and 3 of the drawings, a front housing member 19 of the housing further provides a speed control button 35 an the stroke control button 34. The speed control button 35 is arranged for controlling a suction speed of the cylinder, which in turns control an efficiency and effectiveness of pumping breast milk while providing flexibilities to different user based on their habits. The control circuit detects the output voltage of the potentiometer which is corresponding to a voltage of the DC motor such that a rotational speed is adjusted. The function of the stroke control button 35 is described above.

Referring to FIG. 6 of the drawings, the front housing member 19 further provides a promoting lactation button 33 for fast suction. When the promoting lactation button 33 is pressed, the cylinder is promptly entered into a high frequency and short suction cycle process and is then returned to the speed and suction force level after a preset time period, which is a few seconds in this case. This is to simulate the two stage of breast feed action of a baby. In the first stage, the baby will suck at a high frequency which will stimulate and promote lactation. After a few second, the baby will suck at a low frequency and powerfully, which is the second stage. Accordingly, this is design to fit the need of a user when the need of promoting lactation is required. The promoting lactation button 33 can be pressed for any period of time to fit the need of the user.

As shown in FIG. 1, a buffer spring 15 is provided between the axis support 49 and the gear swing unit 12. The buffer spring 15 is inserted into a gear swing axis 18, having a first end hooking onto a protruded portion of the axis support 49 and a second end hooking onto a protruded block 17 of the gear swing unit. When the gear swing unit 12 push the cylinder to return journey, the buffer spring 15 is compressed such that a buffering effect is provided. The application of the buffer spring 15 can effectively reduce the sudden increase in vibration speed and noise during the return process of the cylinder, thereby the speed of the cylinder is relatively steady through providing a load to the cylinder for both the forward process and the backward return process for providing a stable operation. The compressed spring of the cylinder at the forward process further provides auxiliary pushing force and hence reduces the maximum power of the DC motor.

As shown in FIGS. 1, 2 and 3 of the drawings, the housing is a self-standing construction which is compact in size and utilizes reduced surface area of a tabletop or surface. The housing has two indented portion defining two bottle side support 37, each of which has a semicircular construction, arranged for supporting a side portion of a bottle 58 and a bottle bottom support 36. The bottle bottom support 36 includes a connecting leg 59; and position members 60, 61 which is arranged for inserting into connecting holes 28, 31 of a bottom portion of the housing. The connecting leg 59 has a position hole 62 and a front inclined surface. The bottom housing member 18 of the housing has a marble position groove 30 through which the connecting leg 59 is inserted into for securing into position. When the bottle bottom support 36 is pulled out, the marble inside the marble position groove 30 will bounce, therefore the bottle bottom support 36 is a detachable unit. During carriage, the bottle bottom support 36 can be detached to minimize a size of the housing for packing. The detached bottle bottom support 36 can also be placed on top of a surface for supporting a positioning of a bottle 58.

The control method according to the preferred embodiment of the present invention employs a control of the DC motor through voltage and speed adjustment. Two inputs of the potentiometer are arranged for adjusting a speed of the DC motor and for adjusting a process of the cylinder respectively. The main MCU has an integrated AD. The PWM driving circuit is mainly responsible for adjusting the speed of the DC motor in which a high power FET is employed. The driving circuit of DC motor employs a high power DARLINGTON tube for assembling H-bridge circuit. The use of DARLINGTON tube is to ratify the limited driving force of single chip processor and to minimize interferences with the DC motor.

According to the preferred embodiment of the present invention, voltage and speed control are employed in consideration of the followings. The power of DC motor is not large. The need of steady rotation of motor. The need of noise reduction. PWM is ideal for providing high efficiency with reduced level of heat generation, however, when PWM is used for speed management, motor is unable to operate in a steady or stable condition while noise level of the motor is increased. Accordingly, voltage and speed management is used in the preferred embodiment of the present invention.

Three photoelectric sensor input are employed, namely near position photoelectric sensor, far position photoelectric sensor and DC motor counting photoelectric sensor. The three photoelectric sensors are arranged for providing output into I/Os of the single chip processor such that the single chip processor monitors on a real-time basis. The power supply includes two sources, which are internal power supply and external power supply to a relay through a resettable fuse respectively, for monitoring and control. In order to avoid interferences between the two sources, only one power source can be used at any one time.

MCU is installed to control the process motion to avoid the piston being stuck with the cylinder. When the suction force is too large, motor will be stalled and the piston cannot be pulled into motion, while a large and continuous suction force may cause damage to a nipple. A timing process for preventing motor blockage will provide protection effect through releasing the suction force after a preset time period, preferably within a few second, through controlling a reverse rotational motion of the motor.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A piston-type breast pump which includes a housing and a piston-type pumping arrangement received in the housing, comprising:
    a DC motor, a gear reducer and a control circuit which are received in the housing;
    a gear swing unit operatively communicated with said gear reducer and connected to said pumping arrangement;
    first and second position sensor plates for detecting a far point position and a near point position respectively provided between said gear swing unit and said gear reducer;
    a buffer spring connected to said gear swing unit;
    a stroke sensor wheel positioned on an axis member of said DC motor; and
    a speed control button, stroke control button, a promoting lactation button and a suction adjustment screw positioned on an outer side of said housing;
    wherein said housing has a vertical design having an indented portion defining a bottle side support on said housing and comprising a bottle bottom support provided thereon in a detachable manner.

2. A piston-type breast pump, as recited in claim 1, wherein said housing comprises a front housing member, a rear housing member and a bottom housing member for forming said housing, wherein said speed control button, said stroke control button and said promoting lactation button are provided on said front housing member and communicatively connected to said control circuit, wherein said bottle side support is constructed into a semicircle structure having a bottom end operatively connected with said bottle bottom support for retaining a milk bottle into position, wherein said front housing member further provides an output head arranged for connecting to the milk bottle through a bottle connecting tube, wherein said suction adjustment screw is positioned on said rear housing member.

3. A piston-type breast pump, as recited in claim 2, wherein said gear reducer comprises an axis support connected to said bottom housing member; a first axis, a second axis, a gear swing core axis positioned and supported in sequence through an inclined surface defined through a supporting side of said axis support; a gear connected to a middle portion of said first axis; a gear pulley connected to an end portion of said first axis; a second gear provided to a middle portion of said second axis operatively connected to said gear of said first axis, a third gear provided at one end portion of said second gear complementary to a teeth surface of said gear swing unit; a gear swing axis provided at one end of said gear swing unit through which said piston-typed pumping arrangement is connected; a motor pulley connected to said gear pulley through a belt arranged for connecting said gear pulley to said DC motor, wherein said gear has a size smaller than said second gear, and said second gear has a size larger than said third gear.

4. A piston-type breast pump, as recited in claim 3, wherein said buffer spring is inserted to connecting to said gear swing core axis in an enclosed manner, wherein said buffer spring has two ends defining to force receiving portions which are provided to said gear swing unit and to said axis support respectively.

5. A piston-type breast pump, as recited in claim 3, further comprising two photoelectric sensors positioned corresponding to said first and second position sensor plates respectively in which said first and second position sensor plates have a protruded structural construction.

6. A piston-type breast pump, as recited in claim 3, wherein said stroke sensor wheel and said motor pulley are connected, wherein said stroke sensor wheel has two indented portions, wherein said stroke sensor wheel comprises photoelectric sensor corresponding to said stroke sensor wheel on an outer side of said stroke sensor wheel.

7. A piston-type breast pump, as recited in claim 2, further comprising a frame unit connected to said bottom housing member and a control valve support through and provided on said frame unit, wherein said piston-typed pumping arrangement comprises a cylinder defining a cylinder cavity, a piston unit operatively provided in said cylinder cavity; and an output tube and a connecting output provided at one end portion of said cylinder, wherein said output tube is connected to an output head of said front housing member, wherein said end portion of said cylinder is connected to said frame unit in a hinged manner, wherein said control valve is connected to said connecting output through said output tube.

8. A piston-type breast pump, as recited in claim 7, wherein said control valve has a valve body, a valve core and a suction adjustment screw for forming said control valve, wherein said valve core has a cone structure at a first end and a plurality of thread construction at second end opposite to said first end, wherein said valve body has a core receiving cavity arranged for receiving and connecting said valve core, wherein said valve body has an input opening and an output opening which are channeled through said core receiving cavity respectively, wherein said valve body is supported by said frame unit, wherein said suction adjustment screw is connected with said valve core and extended to penetrate to an outer side of said rear housing member, wherein said input opening is connected to said connecting output through a tube.

9. A piston-type breast pump, as recited in claim 2, wherein said bottle bottom support comprises a connecting leg and a position member, wherein said housing has a position groove and a connecting hole corresponding to a position of said connecting leg and said position member respectively, wherein said connecting leg has a position hole and an inclined surface provided thereon.

10. A piston-type breast pump, as recited in claim 1, wherein said gear reducer comprises an axis support connected to said bottom housing member; a first axis, a second axis, a gear swing core axis positioned and supported in sequence through an inclined surface defined through a supporting side of said axis support; a gear connected to a middle portion of said first axis; a gear pulley connected to an end portion of said first axis; a second gear provided to a middle portion of said second axis operatively connected to said gear of said first axis, a third gear provided at one end portion of said second gear complementary to a teeth surface of said gear swing unit; a gear swing axis provided at one end of said gear swing unit through which said piston-typed pumping arrangement is connected; a motor pulley connected to said gear pulley through a belt arranged for connecting said gear pulley to said DC motor, wherein said gear has a size smaller than said second gear, and said second gear has a size larger than said third gear.

11. A piston-type breast pump, as recited in claim 10, wherein said buffer spring is inserted to connecting to said gear swing core axis in an enclosed manner, wherein said buffer spring has two ends defining to force receiving portions which are provided to said gear swing unit and to said axis support respectively.

12. A piston-type breast pump, as recited in claim 10, further comprising two photoelectric sensors positioned corresponding to said first and second position sensor plates respectively in which said first and second position sensor plates have a protruded structural construction.

13. A piston-type breast pump, as recited in claim 10, wherein said stroke sensor wheel and said motor pulley are connected, wherein said stroke sensor wheel has two indented portions, wherein said stroke sensor wheel comprises photoelectric sensor corresponding to said stroke sensor wheel on an outer side of said stroke sensor wheel.

14. A piston-type breast pump, as recited in claim 1, further comprising a frame unit connected to said bottom housing member and a control valve support through and provided on said frame unit, wherein said piston-typed pumping arrangement comprises a cylinder defining a cylinder cavity, a piston unit operatively provided in said cylinder cavity; and an output tube and a connecting output provided at one end portion of said cylinder, wherein said output tube is connected to an output head of said front housing member, wherein said end portion of said cylinder is connected to said frame unit in a hinged manner, wherein said control valve is connected to said connecting output through said output tube.

15. A piston-type breast pump, as recited in claim 14, wherein said control valve has a valve body, a valve core and a suction adjustment screw for forming said control valve, wherein said valve core has a cone structure at a first end and a plurality of thread construction at second end opposite to said first end, wherein said valve body has a core receiving cavity arranged for receiving and connecting said valve core, wherein said valve body has an input opening and an output opening which are channeled through said core receiving cavity respectively, wherein said valve body is supported by said frame unit, wherein said suction adjustment screw is connected with said valve core and extended to penetrate to an outer side of said rear housing member, wherein said input opening is connected to said connecting output through a tube.

16. A piston-type breast pump, as recited in claim 1, wherein said bottle bottom support comprises a connecting leg and a position member, wherein said housing has a position groove and a connecting hole corresponding to a position of said connecting leg and said position member respectively, wherein said connecting leg has a position hole and an inclined surface provided thereon.

* * * * *